United States Patent [19]

Botich et al.

[11] Patent Number: 6,039,713
[45] Date of Patent: Mar. 21, 2000

[54] PRE-FILLED RETRACTABLE NEEDLE INJECTION DEVICE

[75] Inventors: Michael J. Botich, Oxnard; Thor R. Halseth, Simi Valley; John Barker, Ventura, all of Calif.

[73] Assignee: MDC Investment Holdings, Inc., Wilmington, Del.

[21] Appl. No.: 09/139,540

[22] Filed: Aug. 26, 1998

Related U.S. Application Data

[60] Provisional application No. 60/078,233, Mar. 17, 1998, and provisional application No. 60/058,004, Aug. 28, 1997.

[51] Int. Cl.⁷ ........................................ A61M 5/00
[52] U.S. Cl. .................... 604/110; 604/195; 604/187; 604/201; 604/203; 604/231
[58] Field of Search .................... 604/110, 181, 604/187, 195, 231–234, 200, 201, 203, 205, 218, 220, 244, 221

[56] References Cited

U.S. PATENT DOCUMENTS

| 4,445,895 | 5/1984 | Margulies . |
| 4,747,829 | 5/1988 | Jacob . |
| 4,767,413 | 8/1988 | Haber . |
| 4,808,169 | 2/1989 | Haber . |
| 4,826,489 | 5/1989 | Haber . |
| 4,900,307 | 2/1990 | Kulli . |
| 4,909,794 | 3/1990 | Haber . |
| 4,919,657 | 4/1990 | Haber . |
| 4,927,414 | 5/1990 | Kullli . |
| 4,994,034 | 2/1991 | Botich . |
| 5,019,052 | 5/1991 | Rohrbough ............................. 604/203 |
| 5,053,010 | 10/1991 | McGray et al. ....................... 604/110 |
| 5,167,641 | 12/1992 | Schmitz . |
| 5,188,599 | 2/1993 | Botich . |
| 5,330,430 | 7/1994 | Sullivan ................................ 604/134 |
| 5,407,431 | 4/1995 | Botich . |
| 5,423,758 | 6/1995 | Shaw . |
| 5,520,642 | 5/1996 | Bigagli et al. ........................ 604/88 |
| 5,593,391 | 1/1997 | Stanners . |
| 5,632,733 | 5/1997 | Shaw ................................... 604/195 |
| 5,685,863 | 11/1997 | Botich . |
| 5,788,677 | 8/1998 | Botich et al. ........................ 604/195 |
| 5,800,395 | 9/1998 | Botich . |

*Primary Examiner*—Corrine McDermott
*Assistant Examiner*—Cris L. Rodriguez
*Attorney, Agent, or Firm*—Dann, Dorfman, Herrell and Skillman; Stephen H. Eland

[57] ABSTRACT

A needle-bearing device for injecting medicinal fluid from a pre-filled cartridge is provided. After use, the needle is retracted into the body of the device to prevent inadvertent contact with the sharpened end of the needle. In one embodiment, the invention provides a manually actuable button that effectuates retraction of the needle after use. In another embodiment, retraction is effectuated automatically after the injection is complete.

21 Claims, 6 Drawing Sheets

PRE-FILLED RETRACTABLE NEEDLE INJECTION DEVICE

RELATED APPLICATIONS

This application claims priority under 35 U.S.C. §119 to U.S. Provisional Application No. 60/058,004 entitled "Pre-Filled Retractable Needle Injection Device" filed Aug. 28, 1997 and U.S. Provisional Application No. 60/078,233 entitled "Pre-Filled Retractable Needle Injection Device" filed Mar. 17, 1998, each of which applications are hereby incorporated herein by reference.

FILED OF THE INVENTION

The present invention relates to pre-filled ampoules, carpules, or cartridges for administering injections of medicinal fluids to patients. More specifically, the invention relates to such devices having a retractable needle feature for rendering the device non-reusable and safely disposable.

BACKGROUND OF THE INVENTION

Various types of medical devices employ a needle for piercing the skin of a patient for diagnostic or therapeutic purposes. One such device is a cartridge injector. Cartridge injectors utilize pre-filled cartridges that have a pre-measured dose of medication. The cartridge injector is used to inject the medication from the cartridge into a patient.

Handling of such needle-bearing medical devices after the needle is withdrawn from the patient can result in transmission of various pathogens, most notably human immune virus (HIV), to uninfected medical personnel, due to an inadvertent needle stick. Accordingly, it is desirable to provide a device for injecting medication from a pre-filled cartridge, wherein the injection needle is retracted into the housing of the device after use.

DESCRIPTION OF THE DRAWINGS

All of the objects of the present invention are more fully set forth hereinafter with reference to the accompanying drawings, wherein.

DESCRIPTION OF THE PREFERRED EMBODIMENT

Figure 1A:
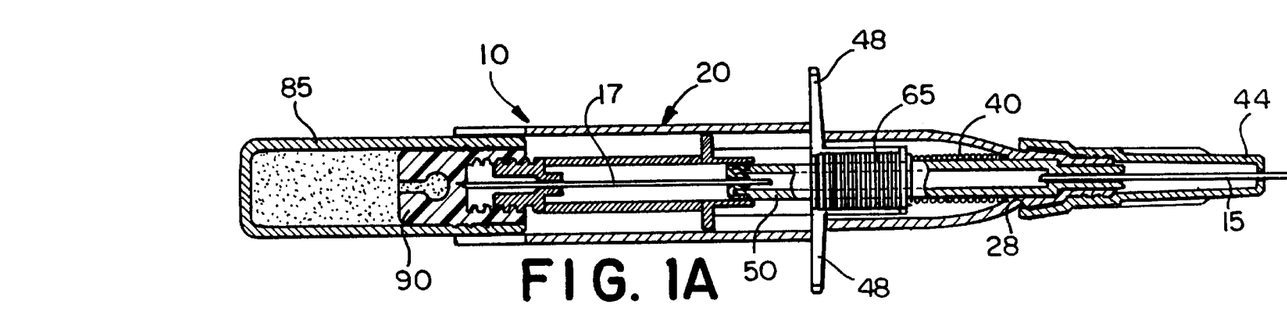
FIG. 1A is a plan view of a cartridge injector embodying aspects of the present invention.
Figure 1B:
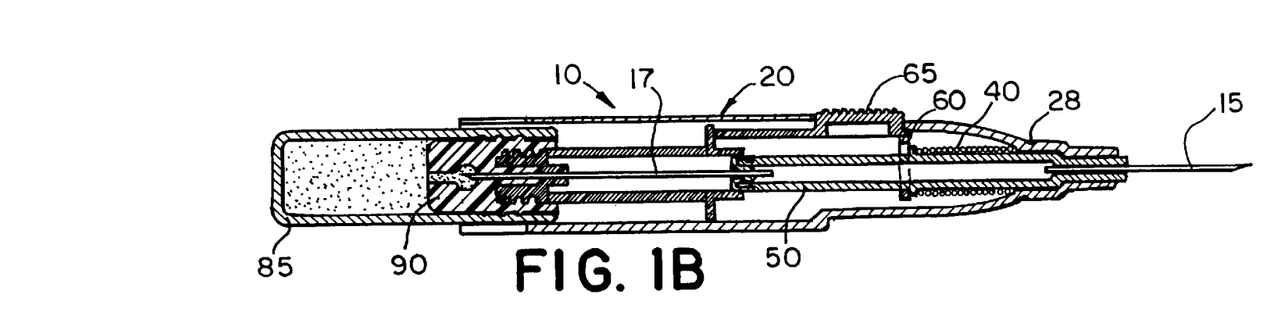
FIG. 1B is a side view of the cartridge injector shown in FIG. 1A, illustrated without a needle cap.
Figure 1C:
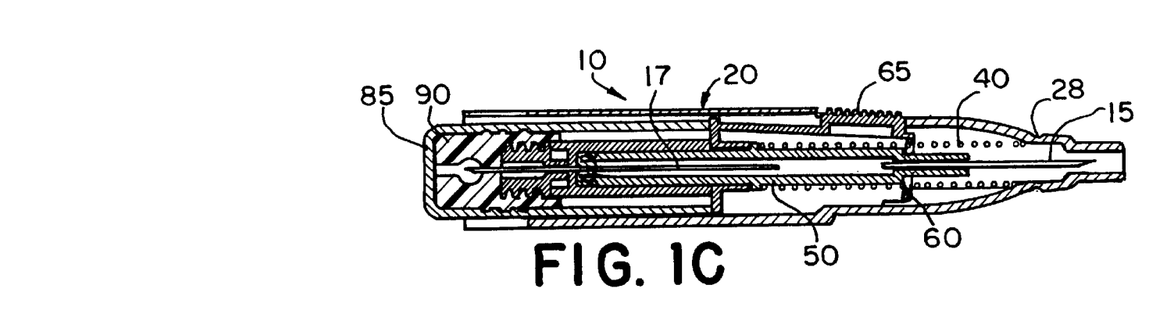
FIG. 1C is a side view of the cartridge injector shown in FIG. 1B, showing the needle retracted.

Referring now to the drawings in general, and FIGS. 1A–1C specifically, there is shown a cartridge injector 10 with an attached cartridge 85 pre-filled with medication. The cartridge injector 10 includes a front needle 15 with a sharpened tip for inserting the needle into a patient. The front needle 15 is in fluid communication with the medicine in the cartridge 85. By pressing the cartridge 85 into the cartridge injector 10, the medicine is expelled from the cartridge and into the patient through the front needle 15. After the medicine is administered to the patient, the front needle 15 is retracted into the body of the cartridge injector by depressing an actuator button 65.

Figure 2:
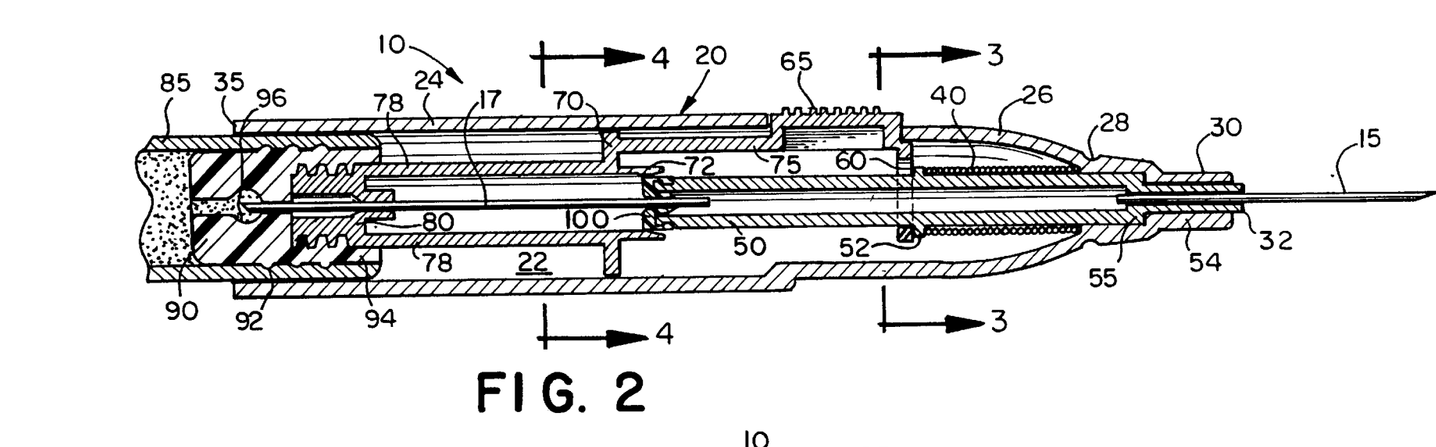
FIG. 2 is an enlarged fragmentary cross-sectional view of the cartridge injector illustrated in FIG. 1B.

Referring now to FIG. 2, the details of the cartridge injector 10 are illustrated. The cartridge injector 10 includes a hollow body or housing 20 having an internal cavity 22. The housing 20 includes a cylindrical barrel 24. The rearward end of the barrel 24 is open, forming a cylindrical socket 35 for receiving the cartridge 85. As shown in FIG. 1A, two laterally extended flanges 48 project outwardly from the barrel 24, transverse the axis of the barrel, forming two finger grips for operating the device. Referring again to FIG. 2, the forward end of the housing 20 convergingly tapers, forming a nose 26 that is integrally connected to the barrel 24. The forwardmost end of the nose 26 is axially elongated forming a hollow cylindrical tip 30.

The nose tip 30 has an opening 32 through which the front needle 15 projects outwardly from the body 20 so that the sharpened tip of the needle can be inserted into a patient for administering medication to the patient. As shown in FIG. 1A, prior to use, a needle cap 44 encloses the portion of the front needle 15 projecting from the housing. The needle cap 44 snaps onto the nose 26 and is frictionally retained by the interface between an external circumferential groove 28 on the nose and a corresponding internal circumferential rim on the base of the needle cap.

As shown in FIG. 2, the cartridge injector 10 includes two needles: the front needle 15 for being inserted into the patient; and a rear needle 17 for piercing the cartridge 85. A conduit 50 extends between the front needle 15 and the rear needle 17 so that the two needles are in fluid communication. The conduit 50 is a cylindrical tube. The rear end of the conduit 50 is generally open, and the forward end of the conduit has a reduced diameter cylindrical tip 54. The bore of the tip 54 is sized to receive the front needle 15. The front needle 15 is fixedly retained in the bore of the conduit tip 54, preferably by bonding. Alternatively, the front needle 15 can be fixed to the conduit tip 54 by interference fit or by molding the front needle into the conduit tip.

The cylindrical conduit tip 54 is inserted into the bore of the housing tip 30 so that the front needle 15 projects from the housing 20. The external surface of the conduit tip 54 corresponds to the inner bore of the nose tip 30 so that the conduit tip is slidably engaged within the nose tip. The intersection of the conduit tip 54 and the larger diameter of the conduit 50 forms an external circumferential shoulder 55. The conduit shoulder 55 abuts a corresponding annular shoulder formed in the interior of the housing nose 26.

Figure 5:
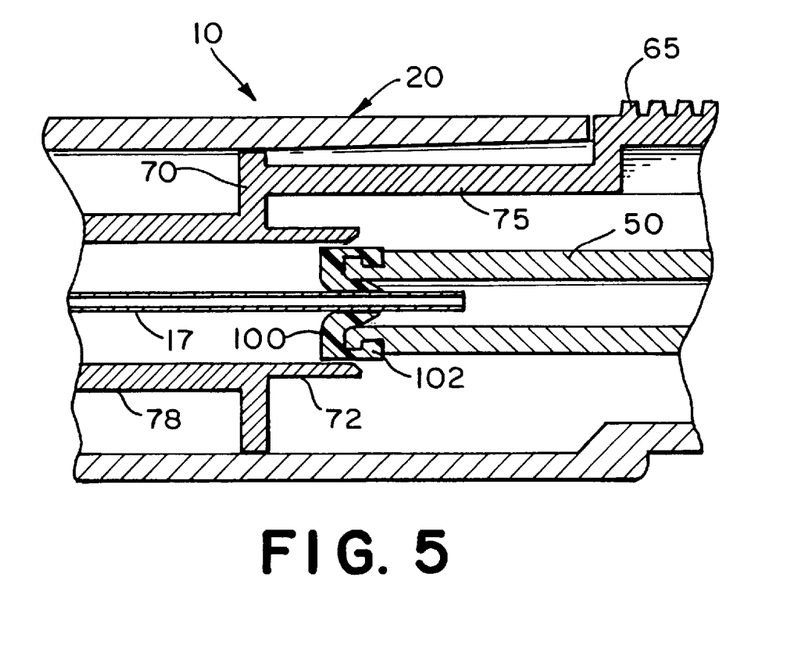
FIG. 5 is an enlarged fragmentary cross-sectional view of the cartridge injector shown in FIG. 2, illustrating the details of the rear needle seal.

The rearward end of the conduit 50 is supported by a disk-shaped hub 70 in the barrel 24. The hub 70 includes an annular flange 72 that projects forwardly from the hub creating a socket for receiving the rearward end of the conduit 50. A flexible seal 100 provides a fluid-tight seal between the conduit 50 and the hub socket 72. The seal 100 is generally cup-shaped and is disposed about the rearward end of the conduit. The open end of the cup-shaped seal 100 includes a radially-inwardly-extending circumferential flange 102 forming a rim that seats in a groove at the rearward end of the conduit. The seal 100 further includes a bore sized for receiving the rear needle 17, to form a fluid-tight seal with the rear needle. As shown in FIG. 5, the seal 100 projects into the conduit 50 around the rear needle 17 forming a fluid-tight seal between the side of the rear needle and the bore of the conduit.

Figure 4:
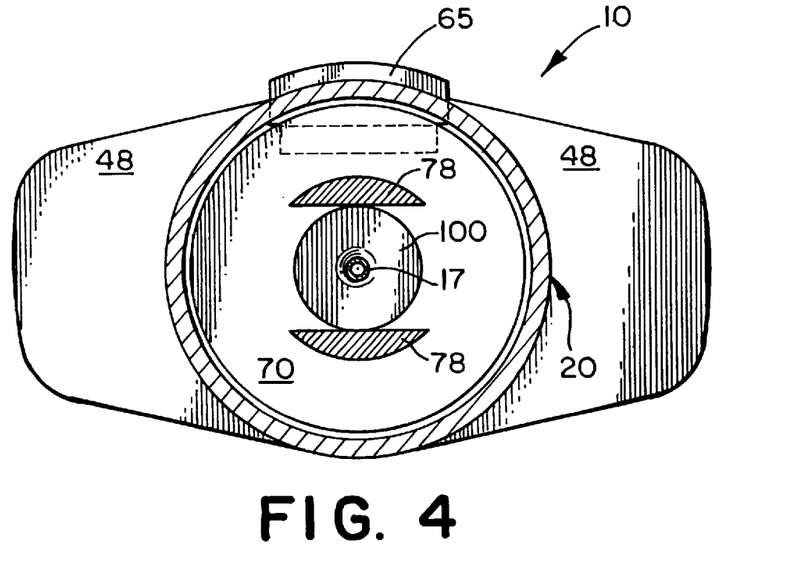
FIG. 4 is an enlarged cross-sectional view of the cartridge injector shown in FIG. 2, taken along line 4—4.

As shown in FIG. 2, the forward end of the rear needle 17 extends through the seal 100 and projects into the bore of the conduit 50. The rearward end of the rear needle 17 extends through and is fixedly connected to a mounting stem 80. The mounting stem 80 has an internal bore for retaining the rear needle. In addition, the mounting stem is adapted to be releasably connectable to the cartridge 85. A plurality of axially elongated support rods 78 connect the mounting stem 80 to the hub 70. As shown in FIG. 4, preferably the support rods 78 are laterally elongated to provide increased torsional rigidity; however, the connecting rods can alternatively be cylindrical.

Referring again to FIG. 2, the rearward end of the housing 35 is generally opened, forming a socket for receiving the cartridge 85. The cartridge 85 is a generally cylindrical vessel containing an amount of medicinal fluid. The rearward end of the cartridge 85 is closed, and the forward end of the cartridge is sealed by a rubber piston or plug 90. The plug 90 is generally cylindrical having a plurality of axially-spaced circumferential ribs 92 that form a fluid-tight seal between the plug 90 and the internal surface of the cartridge 85.

The forward or external end of the plug is configured to cooperate with the mounting stem 80 of the cartridge injector. In the present instance, the mounting stem 80 is externally threaded and the plug 90 has corresponding internal threads 94. The interior end of the plug 90 adjacent the medication includes a recess 96. In this way, a pierceable wall is formed in the plug 90 between the recess 96 and the base of the internal threads 94. When the cartridge 85 is mounted on the mounting stem 80, the rear needle 17 pierces the wall of the plug and extends into the recess 96 formed in the interior of the plug. The recess opens to the interior of the cartridge 85 so that when the rear needle 17 projects into the recess 96, the rear needle is in fluid communication with the interior of the cartridge 85, allowing medication to flow from the cartridge into the rear needle. After the rear needle 17 pierces the wall of the plug, the wall forms a fluid-tight seal between the plug 90 and the side of the rear needle to prevent medication from leaking into the housing 20.

The medication is expelled from the cartridge 85 by moving the cartridge 85 axially forwardly to advance the cartridge. The plug 90 is mounted on the mounting stem 80 so that the plug remains stationary while the cartridge 85 is advanced. The plug 90 is configured to form a sliding fit with the interior of the cartridge so that the cartridge 85 can slide over the plug to expel the medication from the cartridge.

Additionally, the circumferential ribs 92 maintain a fluid-tight seal between the piston and the cartridge while the cartridge slides over the piston.

As the cartridge 85 is advanced, the medication in the cartridge flows out of the cartridge and into the rear needle 17. From the rear needle 17, the medication flows into the conduit 50 and then out the front needle 15 into the patient. After the medication is injected into the patient, the front needle 15 can be retracted into the housing 20 as follows.

A spring 40 is disposed around the conduit 50, biasing the conduit rearwardly. The forward end of the spring 40 abuts against the interior of the nose 26, and the rearward end of the spring abuts against a circumferential flange or rim 52 formed around the outer surface of the conduit 50. The rim 52 engages a latch 60 that is connected to an actuator button 65. Pressing the actuator button 65 releases the rim 52 of the conduit 50 from the latch 60 so that the spring 40 propels the conduit and the attached front needle 15 rearwardly. When the conduit 50 and the needle 15 are propelled rearwardly, the rear end of the conduit 50 slides through the hub socket 72 and over the rear needle 17. In addition, when the conduit 50 retracts rearwardly, the needle seal 100 also retracts rearwardly over the rear needle 17 and through the hub socket 72. Therefore, to facilitate retraction, the seal 100 forms a sliding fit with both the rear needle 17 and the socket hub 72. Additionally, the seal 100 seals the internal cavity 22 of the housing 20 from communicating with the fluid in rear needle 17 and the conduit 50.

Figure 3:
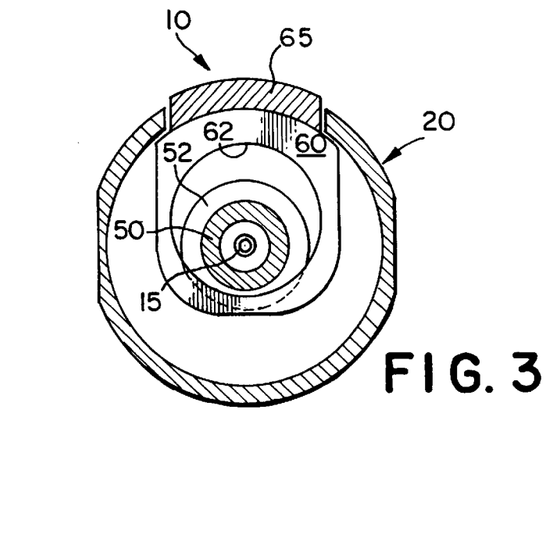
FIG. 3 is an enlarged cross-sectional view of the cartridge injector illustrated in FIG. 2, taken along line 3—3.

The details of the latch 60 that retains the conduit and the front needle 15 in the extended position are best seen in FIG. 3. The latch 60 has a circular aperture 62 that is larger in diameter than the diameter of the rim 52 around the conduit 50. The latch aperture 62 is eccentric with the conduit 50, so that the conduit rim 52 interferes with the latch 60 as shown in FIG. 3. By pressing the actuator button 65 downwardly, the latch aperture 62 is aligned with the conduit rim 52 so that the conduit rim can pass through the latch aperture, allowing the conduit 50 and attached needle 15 to retract into the housing 20.

Referring again to FIG. 2, the latch 60 is integrally connected to the actuator button 65. The actuator button 65 is connected to the hub 70 by a cantilever arm 75, so that the actuator button is pivotable about the hub. Preferably, the cantilever arm 75 biases the actuator button 65 upwardly so that the latch 60 is biased upwardly toward the latched position shown in FIG. 3.

Configured in this way, the cartridge injector 10 operates as follows. A cartridge 85 containing medication is inserted into the rearward end 35 of the housing and the cartridge plug 90 is threaded onto the mounting stem 80. When the cartridge plug 90 is threaded onto the mounting stem 80, the rear needle 17 punctures the rear wall of the plug 90 so that the rear needle is in fluid communication with the medication in the cartridge 85. The needle cap 44 is then removed to expose the sharpened tip of the front needle 15. The front needle 15 is inserted into a patient and the cartridge 85 is advanced relative to the stationary plug 90 to inject the medication from the cartridge into the patient. After the injection is complete, the operator can depress the actuator button 65 to release the rim 52 from the latch 60 that retains the conduit 50. The spring 40 then propels the conduit 50 and the front needle 15 rearwardly until the front needle is completely enclosed within the housing 20 as shown in FIG. 1C. Because the operator controls the retraction of the needle by depressing the actuator button 65, the needle can be retracted regardless of whether all of the medication has been expelled from the cartridge. This allows the operator to control the amount of medication injected into the patient, while still allowing the front needle 15 to be retracted into the housing 20.

Figure 6:
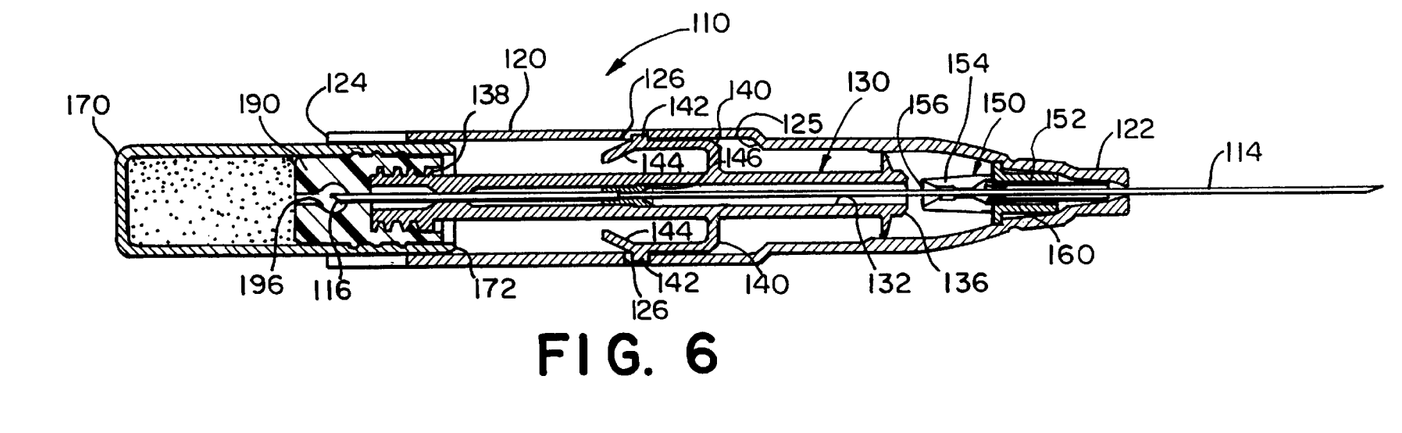
FIG. 6 is a cross-sectional view of an alternate embodiment of a medical device for use in injecting medication from a cartridge.

Referring now to FIGS. 6–11 in general, and to FIG. 6 specifically, an alternate embodiment of a cartridge injector 110 is shown. The alternate embodiment incorporates a needle that is automatically retracted at the end of an injection without manually depressing a separate button. The cartridge injector 110 includes two needles, an insertion needle 114 and a rearward needle 116 that pierces a plug 190 that seals the cartridge 170. The insertion needle 114 is operable to inject medication into a patient, and is releasably retained by a needle retainer 150. An actuator 130 cooperates with the needle retainer 150 such that forward axial displacement of the actuator 130 causes the needle retainer 150 to release the insertion needle 114. A spring 160 then propels the insertion needle 114 rearwardly so that the sharpened tip of the needle is located within the cartridge injector.

The cartridge injector 110 includes a generally cylindrical hollow barrel 120 having a forward reduced diameter tip 122. The tip 122 is generally closed having a orifice through which the insertion needle 114 projects. The rearward end 124 of the barrel 120 is generally open and is sized to receive the cartridge 170.

The needle retainer 150 is positioned within the forward end of the barrel 120, adjacent the tip 122. The needle retainer 150 releasably retains the insertion needle 114 so that the insertion needle projects forwardly from the barrel 120 as illustrated in FIG. 6. The needle retainer 150 can be attached to the barrel 120 in a variety of ways, including ultrasonic welding, epoxy, or a snap fit. In the present instance, the needle retainer 150 is attached to the barrel 120 by way of a snap fit.

The insertion needle 114 projects through an axial bore in the needle retainer 150. The needle retainer includes a generally cylindrical body portion 152 at the forward end of the needle retainer and a plurality of axially elongated fingers 154 that releasably retain the insertion needle 114. The fingers 154 have radially inwardly directed protrusions forming a constricted portion in the bore of the needle retainer. Preferably, the surface of each protrusion is configured to conform to the outer surface of insertion needle 114 to maintain the needle in axial alignment with the needle retainer 150. The surfaces of the protrusions preferably form a continuous surface within the interior of the needle retainer to improve engagement with the insertion needle.

The fingers 154 are secured or bonded to the outer surface of the insertion needle 114 using an adhesive such as an epoxy. The needle retainer 150 preferably includes four fingers 154, but one or more fingers 154 may be employed depending on such factors as the size of the device and the nature of the biasing member. The exterior of the needle retainer 150 is provided with longitudinal grooves or score lines between the fingers 154 to facilitate separation of the fingers when retraction of the needle is actuated.

Alternatively, the needle retainer 150 can utilize a latching arrangement rather than being releasably bonded to the needle. In the latching arrangement, a block is affixed to the insertion needle 114. The ends of the needle retainer fingers 154 form inwardly directed latches that engage the block to releasably retain the insertion needle.

The needle retainer 150 retains the insertion needle 114 against the rearward bias of a spring 160. In the present instance, the spring is a coil spring that circumscribes the insertion needle 114. As shown in FIG. 6, the forward end of the spring 160 bears against the interior of the barrel tip 122. The rearward end of the spring 160 is attached to the insertion needle 114, preferably by a UV curable adhesive. Alternatively, if the latching arrangement is utilized for the needle retainer 150, then the spring can bear against the block fixed to the needle, if desired.

The cartridge injector 110 includes an actuator 130 that is operable to engage the needle retainer 150 to cause the needle retainer to release the insertion needle 114 so that the spring 160 propels the insertion needle rearwardly. The actuator 130 is an elongated generally cylindrical member having a hollow axial bore 132. The axial bore 132 has two diameters. The forward portion of the axial bore has a major diameter that is larger than the diameter of the rearward portion of the axial bore. The forward end of the actuator 130 is generally open for receiving the rearward end of the insertion needle 114 that extends into the axial bore 132 of the actuator.

A mounting stem 138 is connected to the rearward end of the actuator 130. Preferably, the mounting stem 138 is integrally formed with the actuator 130. In the present instance, the mounting stem 138 includes an externally threaded portion for threadedly engaging a plug 190 in the cartridge 190. A rearward needle 160 for piercing the plug 190 of the cartridge 170 projects rearwardly from the mounting stem 138. The rear needle 116 is fixedly connected to the actuator 130, preferably by a UV curable adhesive. The forward portion of the rear needle 114 projects into the axial bore 132 of the actuator 130. Preferably, the rear needle 114 has an internal bore that is larger than the external diameter of the insertion needle 114. In this way, the insertion needle 114 is slidably displaceable within the rear needle 116.

Figure 10:
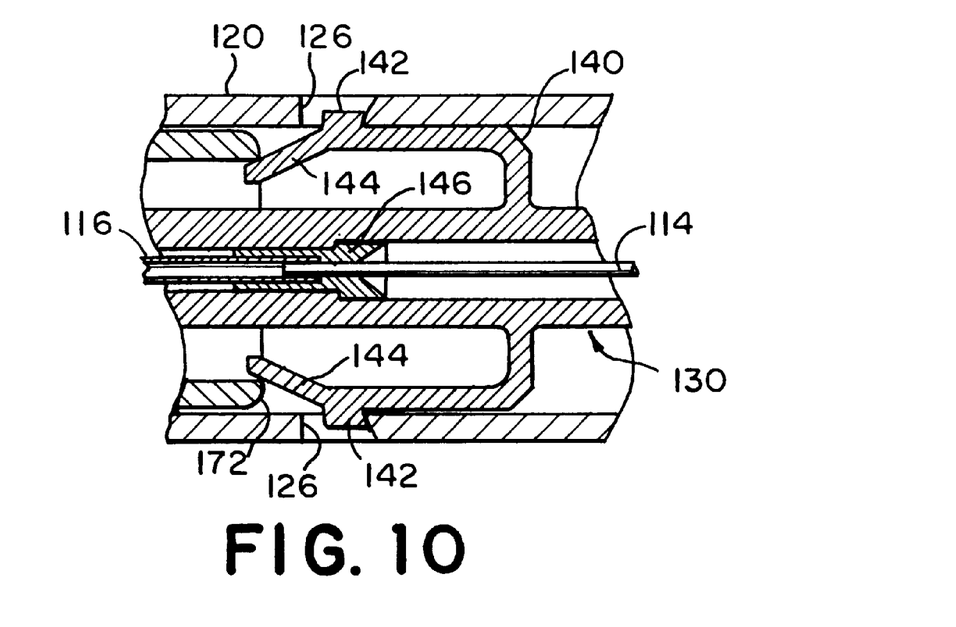
FIG. 10 is an enlarged fragmentary cross-sectional view of the device shown in FIG. 7, illustrating details of the safety latch in a latched position.
Figure 11:
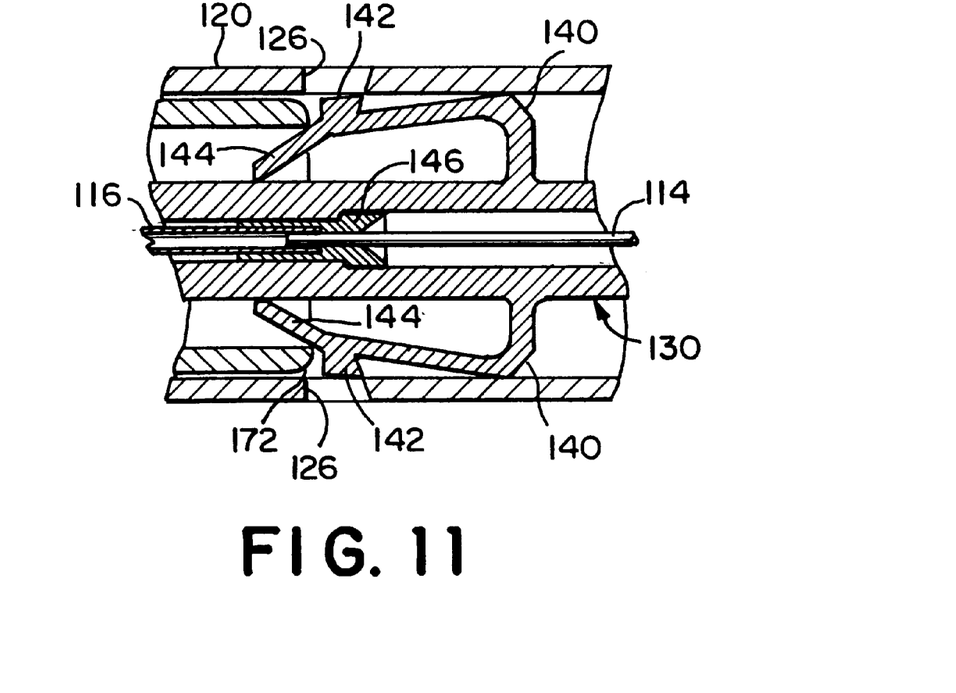
FIG. 11 is an enlarged fragmentary view of the device shown in FIG. 8, illustrating details of the safety latch in an unlatched position.

As shown most clearly in FIG. 10, a seal 146 provides a fluid tight seal between the insertion needle 114 and the rear needle 116. The rear portion of the seal 146 includes a bore sized to receive the forward end of the rear needle 116. The forward portion of the seal 146 includes a constricted portion sized to receive the smaller diameter insertion needle 114, providing a fluid tight seal around the external surface of the insertion needle.

Figure 8:
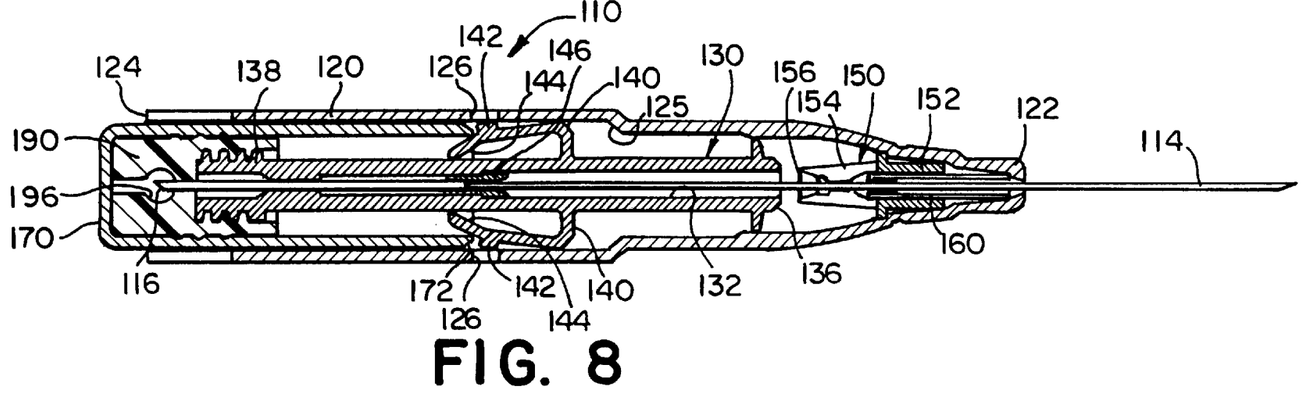
FIG. 8 is a cross-sectional view of the device shown in FIG. 7, illustrating the device in a position just subsequent to release of the safety latch.
Figure 9:
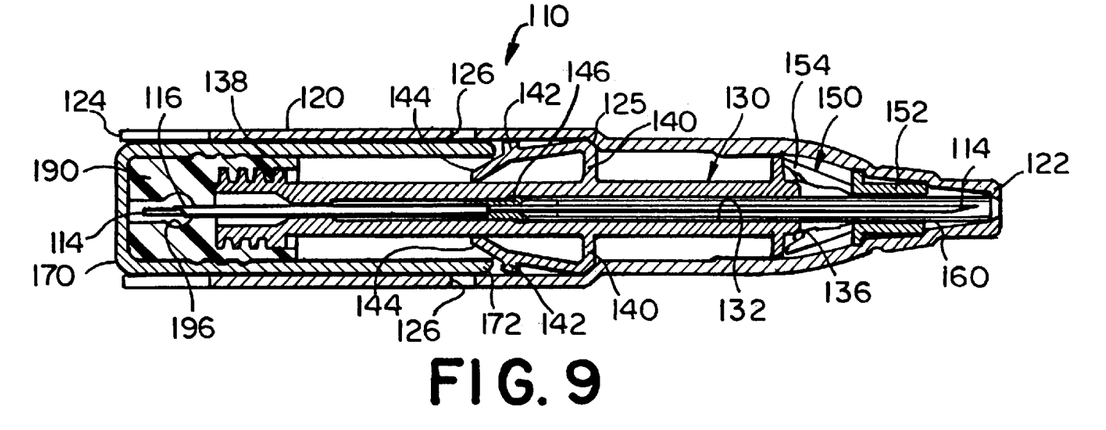
FIG. 9 is a cross-sectional view of the device shown in FIG. 6, illustrating the insertion needle in a retracted position.

The forward end 136 of the actuator 130 is configured to cooperate the rearward end of the fingers 154 of the needle retainer 150. In the present instance, the forward end 136 of the actuator forms a tapered or frustoconical surface. The rearward end of each needle retainer finger 154 tapers radially inwardly so that the rearward end of the needle retainer 150 forms a convergingly tapered annular surface 156. Configured in this way, as shown in FIGS. 8 and 9, when the actuator 130 is axially displaced forwardly to engage the needle retainer 150, the cooperating tapered surfaces of the actuator and the needle retainer operate as a wedge to displace the needle retainer fingers 154 radially outwardly so that the needle retainer releases the insertion needle 114. The spring 160 then propels the insertion needle 114 rearwardly so that the sharpened point of the insertion needle is located within the housing beyond the reach of the operator.

Figure 7:
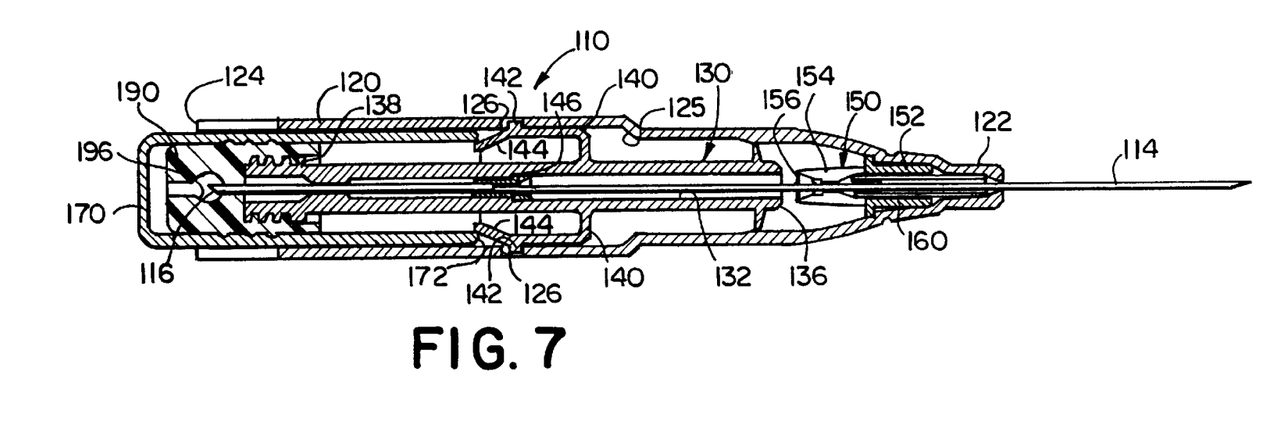
FIG. 7 is a cross-sectional view of the device shown in FIG. 6, illustrating the device in a position just prior to release of a safety latch.

The cartridge injector 110 preferably includes at least one, and preferably two, safety latches 140 that prevent the actuator 130 from being displaced forwardly until some, and preferably substantially all, of the medication is expelled from the cartridge 170. Each safety latch 140 is attached to the actuator 130, and in the present instance, the safety latches are integrally formed with the actuator. Each safety latch 140 is a flexible generally L-shaped arm. The forward end of the safety latch 140 is attached to the actuator 130 and the safety latch extends rearwardly. Each safety latch includes a detent 142 that cooperates with an aperture 126 formed in the wall of the barrel 120. In this way, as shown in FIG. 7, when the detent 142 of the safety latch 140 projects into the aperture 126, the safety latch 140 prevents the actuator 130 from being displaced axially forwardly.

Referring now to FIG. 10, preferably, the forward end of the detent 142 and the forward end of the aperture 126 are matingly tapered to improve the locking engagement of the detent with the aperture. The portion of the safety latch rearward of the detent 142 projects radially inwardly toward the actuator 130, forming a release tab 144. The forward end or rim 172 of the cartridge 170 cooperates with the release tab 144 to release the safety latch 140 as will be discussed further below.

Referring again to FIG. 6, the rearward end of the barrel 120 is generally opened, forming a socket 124 for receiving the cartridge 170. The cartridge 170 is a generally cylindrical vessel containing an amount of medicinal fluid. The rearward end of the cartridge 170 is closed, and the forward end of the cartridge is open forming a rim 172. The open end of the cartridge 170 is sealed by a rubber piston or plug 190. The plug 190 is generally cylindrical having a plurality of axially-spaced circumferential ribs 192 that form a fluid-tight seal between the plug 190 and the internal surface of the cartridge 170.

The forward or external end of the plug is configured to cooperate with the mounting stem 138 of the cartridge injector. In the present instance, the mounting stem 138 is externally threaded and the plug 190 has corresponding internal threads. The interior end of the plug 190 adjacent the medication includes a recess 196. In this way, a piercable wall is formed in the plug 190 between the recess 196 and the base of the internal threads. When the cartridge 170 is mounted on the mounting stem 138, the rear needle 116 pierces the wall of the plug and extends into the recess 196 formed in the interior of the plug. The recess opens to the interior of the cartridge 170 so that when the rear needle 116 projects into the recess 196, the rear needle is in fluid communication with the interior of the cartridge 170, allowing medication to flow from the cartridge into the rear needle. After the rear needle 116 pierces the wall of the plug, the wall forms a fluid-tight seal between the plug 190 and the side of the rear needle to prevent medication from leaking into the barrel 120.

The medication is expelled from the cartridge 170 by moving the cartridge axially forwardly to advance the cartridge. The plug 190 is mounted on the mounting stem 138 so that the plug remains stationary while the cartridge 170 is advanced. The plug 190 is configured to form a sliding fit with the interior of the cartridge so that the cartridge 170 can slide over the plug to expel the medication from the cartridge. Additionally, the circumferential ribs 192 maintain a fluid-tight seal between the plug and the cartridge while the cartridge slides over the plug.

As the cartridge 170 is advanced, the medication in the cartridge flows out of the cartridge and into the rear needle 116. From the rear needle 116, the medication flows into the insertion needle 114 and then into the patient. After the medication is injected into the patient, the insertion needle 114 can be retracted into the housing 120 as follows.

Referring now to FIGS. 7 and 8, when at least substantially all of the medication is expelled from the cartridge 170, the forward rim 172 of the cartridge engages the release tab 144 of each safety latch 140. Continued forward displacement of the cartridge 170 flexes each safety latch 140, displacing the safety latches radially inwardly thereby withdrawing the detents 142 from the apertures 126 in the barrel 120. After the detents 142 are withdrawn from the apertures 126, continued forward displacement of the cartridge 170 displaces the actuator 130 axially forwardly. The actuator 130 then engages the needle retainer 150 to release the insertion needle 114 as shown in FIG. 9 and described previously. In this way, the safety latches 140 prevent the forward axial displacement of the actuator 130 preferably until at least substantially all of the medication is expelled from the cartridge 170. After at least substantially all of the medication has been expelled from the cartridge 170, the safety latch 140 releases the actuator allowing the actuator 130 to engage the needle retainer 150 to release the insertion needle 114.

As shown in FIG. 9, the spring 160 propels the insertion needle 114 rearwardly so that the insertion needle telescopes within the rear needle 116. In addition, as shown in FIG. 9, preferably the barrel 120 includes a reduced diameter forward portion forming an internal annular shoulder 125 that engages the forward portion of the safety latches 140. In this way, the internal shoulder 125 acts as a stop to prevent further forward axial displacement of the actuator.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention. For instance, the second embodiment described above can include a manually actuable release for releasing the safety latches 140 so that the actuator can be actuated to effectuate retraction before substantially all of the medication is expelled from the cartridge. Accordingly, the invention incorporates variations that fall within the scope of the following claims.

That which is claimed is:

1. An injection device for use with a pre-filled medication cartridge of the type containing a supply of medication and having a puncturable piston positioned at a forward end therein, the device comprising:

a barrel sized to receive the cartridge and having a forward portion including a bore of a reduced diameter;

a first needle positioned axially within the reduced diameter portion and extending out of the forward portion of the barrel;

a spring positioned in the barrel for exerting a rearward bias on the needle;

a needle retainer positioned in the barrel for retaining the needle within the bore against the rearward bias exerted by the spring;

a second needle in fluid communication with the medication in the cartridge;

a conduit extending between the first needle and the second needle;

an actuator operable to release the needle from the needle retainer;

wherein the spring propels the conduit and the first needle rearwardly upon release of the needle from the needle retainer so that the conduit telescopingly engages the second needle.

2. A medical device for injecting medication from a cartridge containing medication, wherein the cartridge includes a forward rim, the device comprising:

a housing having an opening for receiving the cartridge;

a first needle projecting forwardly from the housing;

a biasing element biasing the first needle rearwardly;

a needle retainer releasably retaining the first needle against the bias of the biasing elements;

an axially displaceable actuator operable to engage the needle retainer to cause the needle retainer to release the first needle upon forward axial displacement of the actuator;

a latch operable to prevent forward axial displacement of the actuator; and a release cooperable with the rim of the cartridge to displace the latch.

3. The device of claim 2 wherein the cartridge includes a pierceable plug sealing an end of the cartridge and the device comprises a mounting stem for maintaining the plug at a fixed axial position while the medication is expelled from the cartridge.

4. The device of claim 2 wherein the device comprises a second needle that telescopingly engages the first needle.

5. The device of claim 4 comprising a seal providing a fluid-tight seal between the first needle and the second needle.

6. The device of claim 2 wherein the needle retainer comprises a plurality of axially elongated fingers circumferentially spaced apart.

7. The device of claim 2 wherein the actuator comprises a conduit for receiving the medication from the cartridge.

8. The device of claim 2 wherein the rearward end of the needle retainer includes a rearwardly facing tapered actuation surface and the actuator includes a forwardly facing tapered actuation surface that matingly engages the actuation surface of the needle retainer.

9. The device of claim 2 wherein the latch and the release are integrally formed.

10. The device of claim 2 wherein the rim of the cartridge engages the release causing the release to displace the latch to allow displacement of the actuator when at least substantially all of the medication is expelled from the cartridge.

11. A medical device for injecting medication from a cartridge containing medication, wherein the cartridge includes a forward rim, the device comprising:

a housing for receiving the cartridge;

a first needle projecting forwardly from the housing;

retracting means for retracting the first needle into the housing;

retaining means for releasably retaining the first needle from retracting into the housing;

releasing means for releasing the first needle from the means retainer;

safety means for preventing the releasing means from releasing the first needle; and means for overriding the safety means to allow the releasing means to release the needle from the retaining means.

12. The device of claim 11 wherein the cartridge is displaceable within the housing and the safety means is operable in response to displacement of the cartridge.

13. The device of claim 11 wherein the cartridge is displaceable within the housing and the releasing means is operable in response to displacement of the cartridge.

14. The device of claim 11 wherein the cartridge includes a pierceable plug sealing an end of the cartridge and the device comprises a mounting stem for maintaining the plug at a fixed axial position while the medication is expelled from the cartridge.

15. The device of claim 11 wherein the device comprises a second needle that telescopingly engages the first needle.

16. The device of claim 15 comprising a seal providing a fluid-tight seal between the first needle and the second needle.

17. The device of claim 11 wherein the retaining means comprises a plurality of axially elongated fingers circumferentially spaced apart.

18. The device of claim 11 wherein the releasing means comprises a conduit for receiving the medication from the cartridge.

19. The device of claim 11 wherein the rearward end of the retaining means includes a rearwardly facing tapered actuation surface and the releasing means includes a forwardly facing tapered actuation surface that matingly engages the actuation surface of the retaining means.

20. The device of claim 11 wherein the safety means and the means for overriding are integrally formed.

21. The device of claim 11 wherein the rim of the cartridge engages the means for overriding causing the means for overriding to displace the safety means to allow displacement of the releasing means when at least substantially all of the medication is expelled from the cartridge.

* * * * *